US012144610B2

(12) United States Patent
Zou et al.

(10) Patent No.: US 12,144,610 B2
(45) Date of Patent: Nov. 19, 2024

(54) METHOD FOR USER RECOGNITION AND EMOTION MONITORING BASED ON SMART HEADSET (71) Applicant: SHENZHEN UNIVERSITY, Shenzhen (CN)

(72) Inventors: Yongpan Zou, Shenzhen (CN); Haibo Lei, Shenzhen (CN); Kaishun Wu, Shenzhen (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 895 days.

(21) Appl. No.: 17/283,966

(22) PCT Filed: Mar. 4, 2021

(86) PCT No.: PCT/CN2021/079115
§ 371 (c)(1),
(2) Date: Apr. 9, 2021

(87) PCT Pub. No.: WO2021/248942
PCT Pub. Date: Dec. 16, 2021

(65) Prior Publication Data
US 2022/0188392 A1 Jun. 16, 2022

(30) Foreign Application Priority Data

Jun. 12, 2020 (CN) .......................... 202010535561.7

(51) Int. Cl.
*A61B 5/117* (2016.01)
*A61B 5/00* (2006.01)
(Continued)

(52) U.S. Cl.
CPC .............. *A61B 5/117* (2013.01); *A61B 5/165* (2013.01); *A61B 5/6803* (2013.01);
(Continued)

(58) Field of Classification Search
CPC ....... A61B 5/117; A61B 5/165; A61B 5/6803; A61B 5/6843; A61B 5/7203; A61B 5/725;
(Continued)

(56) References Cited

U.S. PATENT DOCUMENTS

| 8,655,004 B2* | 2/2014 | Prest ....................... G06F 3/165 381/380 |
| 2003/0139654 A1* | 7/2003 | Kim ........................ A61B 5/16 600/300 |

(Continued)

FOREIGN PATENT DOCUMENTS

| CN | 102006528 A | 4/2011 |
| CN | 102446533 A | 5/2012 |

(Continued)

*Primary Examiner* — James M Kish
*Assistant Examiner* — Roland Dinga
(74) *Attorney, Agent, or Firm* — Bayramoglu Law Offices LLC (57) ABSTRACT A method for user recognition and emotion monitoring based on a smart headset is provided. The smart headset includes an earplug part and a main body, wherein the earplug part is provided with a first microphone and a wearing detection sensor, and a housing of the main body is provided with a signal amplification circuit, a communication module, and a microcontroller. The wearing detection sensor is to detect whether a user wears the smart headset, and the first microphone is to obtain a sound signal in an ear canal. The sound signal is amplified, and then is outputted to the microcontroller. The amplified sound signal is transmitted by the microcontroller to a smart terminal paired with the smart headset to extract a heart sound signal characteristic, and legality of—identity of the user is validated and emotional state of the user is inferred according to the heart sound signal characteristic.

19 Claims, 4 Drawing Sheets (51) Int. Cl.
*A61B 5/16* (2006.01)
*A61B 7/04* (2006.01)
*H04R 1/08* (2006.01)
*H04R 1/10* (2006.01)
*G06F 21/32* (2013.01)

(52) U.S. Cl.
CPC .......... *A61B 5/6843* (2013.01); *A61B 5/7203* (2013.01); *A61B 5/725* (2013.01); *A61B 5/7267* (2013.01); *A61B 7/04* (2013.01); *H04R 1/083* (2013.01); *H04R 1/1016* (2013.01); *H04R 1/1041* (2013.01); *H04R 1/1075* (2013.01); *H04R 1/1091* (2013.01); *G06F 21/32* (2013.01); *H04R 2201/10* (2013.01)

(58) Field of Classification Search
CPC ........ A61B 5/7267; A61B 7/04; H04R 1/083; H04R 1/1016; H04R 1/1041; H04R 1/1075; H04R 1/1091; H04R 2201/10; G06F 21/32

See application file for complete search history.

(56) References Cited

U.S. PATENT DOCUMENTS

| | | | |
|---|---|---|---|
| 2012/0242501 A1* | 9/2012 | Tran | A61B 5/0024 340/870.02 |
| 2016/0015289 A1* | 1/2016 | Simon | A61B 5/4041 600/301 |
| 2017/0347177 A1* | 11/2017 | Masaki | A61B 5/02028 |
| 2018/0096120 A1* | 4/2018 | Boesen | H04R 1/1016 |
| 2021/0360354 A1* | 11/2021 | Rasmussen | A61B 5/02438 |

FOREIGN PATENT DOCUMENTS

| | | |
|---|---|---|
| CN | 102663457 A | 9/2012 |
| CN | 104338228 A | 2/2015 |
| CN | 111666549 A | 9/2020 |

\* cited by examiner

METHOD FOR USER RECOGNITION AND EMOTION MONITORING BASED ON SMART HEADSET

CROSS REFERENCE TO THE RELATED APPLICATIONS

This application is the national stage entry of International Application No. PCT/CN2021/079115, filed on Mar. 4, 2021, which is based upon and claims priority to Chinese Patent Application No. 202010535561.7, filed on Jun. 12, 2020, the entire contents of which are incorporated herein by reference.

TECHNICAL FIELD

The present disclosure relates to the field of identity authentication and emotion monitoring technologies, and more particularly, to a method for user recognition and emotion monitoring based on a smart headset.

BACKGROUND

With the development of smart wearable devices, headsets are accepted by more and more people. However, the headsets also have privacy functions such as communications and voice chats, to protect user personal information, headset-based identity authentication functions have attracted widespread attention in the industry. At present, there are two main limitations on the headsets, namely, requirements for active interaction, and easiness of being stolen and pilfered. Therefore, user authentication needs to be performed when a smart headset is in use. That is, it is needed to determine whether a user of this headset is a registered user (owner), and after it is determined that the user of this headset is the owner of this headset, it is even further needed to unlock devices such as a mobile phone or a computer paired with this headset. Therefore, the user authentication will satisfy the user's strong demands for product privacy and protection of usage rights, and can significantly improve intelligent autonomy of products.

In addition, as life pressure continues to increase, more and more people are emotionally unstable, depressed for a long time, and suffer from depression, anxiety, etc. Therefore, it is important to timely and continuously monitor emotions and provide emotional relief.

In the existing technologies, technical solutions for implementing the identity authentication mainly include following methods.

1) Identity authentication based on information secrets. That is, identity authentication is performed based on information that the user knows, such as static passwords, etc. This method is simple in use and deployment, but is lower in security, and authentication information is easy to be stolen.

2) Identity authentication based on trusted objects. That is, identity authentication is performed based on information or device owned by the user, such as smart cards, SMS passwords, dynamic passwords, USB KEY, OCL, and Bluetooth locks, etc. Network security of this method is higher than the identity authentication based on information secrets. This method lacks convenience and requires the user to carry the trusted objects. When the trusted objects are accidentally lost, guarantee of security of this method is lost.

3) Identity authentication based on biological characteristics. That is, identity authentication is performed based on biological characteristics such as measurable and unique bodies or behaviors, for example, common retina recognition, iris recognition, fingerprint recognition, palm recognition, face recognition, voice recognition, signature recognition, vascular texture recognition, human odor recognition, DNA recognition, electrocardiograph (ECG) recognition, electroencephalogram (EEG) recognition, etc. This method is convenient, unique and non-reproducible, and has the highest security. However, this method needs large authentication devices, which are inconvenient to carry. Furthermore, a range of application of the authentication devices is limited, and this method cannot be implemented on the smart headsets.

4) Identity authentication for wearable devices based on physiological characteristics and behavioral characteristics. For example, there is a method for identity authentication based on EEG biological characteristics in ears. In this method, electrodes are added into an in-ear part of the headset to collect the EEG, and identity recognition is implemented through a support vector machine categorizer. For the method of collecting the EEG, the main problem is that collecting devices are complicated and collecting conditions are demanding. For example, it is not only required to ensure that the in-ear part of the headset is in perfect contact with the ear canal, but also required to attach an extra electrode to an earlobe part as a reference electrode, which is inconvenient in actual use. For another example, there is also a method for identity authentication using echoes of playing specific audio to obtain unique physical and geometric characteristics of the ear canal. In this method, a microphone is added nearby a speaker of the headset to collect the echoes generated by the ear canal when the audio is played. These echoes contain the unique physical and geometric characteristics of the ear canal. After characteristic extraction is completed, the identity recognition is implemented through the support vector machine categorizer. For the method of audio echo, the main problem is that a specific piece of audio needs to be played first. This piece of audio may be a swept-frequency signal, a fixed-frequency sine wave or a specific audio frequency. However, in either way, the user will be disturbed by the sound being played.

In the existing technologies, technical solutions for implementing emotion monitoring mainly include following methods.

1) Emotion recognition based on facial expressions. This method requires the use of a camera to continuously track changes of facial expressions. This method is expensive, requires active cooperation from users, has privacy issues, and is easy to pretend such that it is unable to detect true internal emotions.

2) Emotion recognition based on speech signals. In this method, semantic contents of speech or rhythms of speakers are analyzed. This method also has the risk of leaking the users' speech contents and is greatly affected by the differences in habits of individual expressing emotions. Furthermore, this method is also easy to pretend such that it is unable to detect true internal emotions, requires the users to speak to provide emotion monitoring, and requires the users to cooperate for use.

3) Emotion recognition based on physiological signals. For example, common physiological signals include electroencephalogram (EEG) signals, electromyography (EMG) signals, skin electric signals, electrocardiograph (ECG) signals, pulse signals, and respiration (RSP) signals, etc. This method is more related to people's internal emotional states. This is because human physiological signals are only dominated by autonomic nervous systems and endocrine systems. However, in order to measure accurate physiological signals, devices used in this method generally are bulky and inconvenient to carry, which hinders the users' daily activities.

4) Emotion recognition based on multiple modalities. This method integrates two or more different signals of the above technologies. Although this method has the advantage of accuracy, it also has the disadvantages of the above methods.

In summary, the devices for identity authentication and emotion monitoring in the existing technologies mainly have the following disadvantages. These devices are inconvenient to carry. It is easy to leak the users' privacies because of poorer information security. These devices have poor robustness, and results of identity authentication and emotion monitoring are not accurate enough, and are susceptible to external factors.

SUMMARY

An objective of the present disclosure is to overcome the defects of the existing technologies by providing a method for user recognition and emotion monitoring based on a smart headset. After a user wears the headset, autonomous identity authentication and emotion monitoring can be implemented.

Technical solutions of the present disclosure are as below. There is provided a method for user recognition and emotion monitoring based on a smart headset. The smart headset includes an earplug part and a main body, the earplug part is provided with a first microphone and a wearing detection sensor, and a housing of the main body is internally provided with a signal amplification circuit, a communication module, and a microcontroller. The wearing detection sensor is configured to detect whether a user wears the headset properly, and the first microphone is configured to obtain a sound signal in an ear canal. The sound signal is amplified by the signal amplification circuit, and then the amplified sound signal is outputted to the microcontroller. The amplified sound signal is transmitted by the microcontroller via the communication module to a smart terminal paired with the smart headset to extract a heart sound signal characteristic, and legality of the user's identity is validated and the user's current emotional state is inferred according to the heart sound signal characteristic.

Compared with the existing technologies, advantages of the present disclosure are as below. In addition to providing functions of a general headset, the smart headset system provided by the present disclosure can also autonomously perform identity authentication and emotion monitoring after the user wears the headset, which not only can protect the user's privacy but also can continuously track the user's internal emotions in real time. Furthermore, the smart headset is lower in hardware costs and convenient for use, and can accurately and quickly perform identity authentication and can continuously perform emotion monitoring during application.

Other characteristics and advantages of the present disclosure will become apparent from the following detailed description of exemplary embodiments of the present disclosure with reference to accompanying drawings.

BRIEF DESCRIPTION OF THE DRAWINGS

The accompanying drawings herein are incorporated in and constitute a part of this specification, illustrate embodiments of the present disclosure and, together with the specification, serve to explain the principles of the present disclosure.

DETAILED DESCRIPTION OF THE EMBODIMENTS

Various exemplary embodiments of the present disclosure will now be described in detail with reference to the accompanying drawings. It is to be noted that the relative arrangement, numerical expressions, and numerical values of the components and steps set forth in these embodiments do not limit the scope of the present disclosure unless otherwise specifically stated.

The following description of at least one exemplary embodiment is actually merely illustrative, and in no way serves as any limitation on the present disclosure and application or use thereof.

Technologies, methods and equipment known to those of ordinary skill in the related art may not be discussed in detail, but where appropriate, the technologies, methods and equipment should be considered as part of the specification.

In all examples shown and discussed herein, any specific values should be interpreted as merely exemplary and not limiting. Therefore, other examples of the exemplary embodiment may have different values.

It is to be noted that similar reference numerals and letters indicate similar items in the following accompanying drawings. Therefore, once an item is defined in one drawing, there is no need to discuss this item further in subsequent drawings.

The smart headset provided by the embodiments of the present disclosure may be of different types or forms. For example, the smart headset may be an in-ear, ear-hanging or neck-hanging headset. The smart headset as a whole includes an earplug part and a headset body. The earplug part includes a speaker and a microphone, etc. The headset body includes a housing, a key or touch panel arranged on the housing, and a circuit board encapsulated in an inner cavity of the housing, etc.

Figure 1:
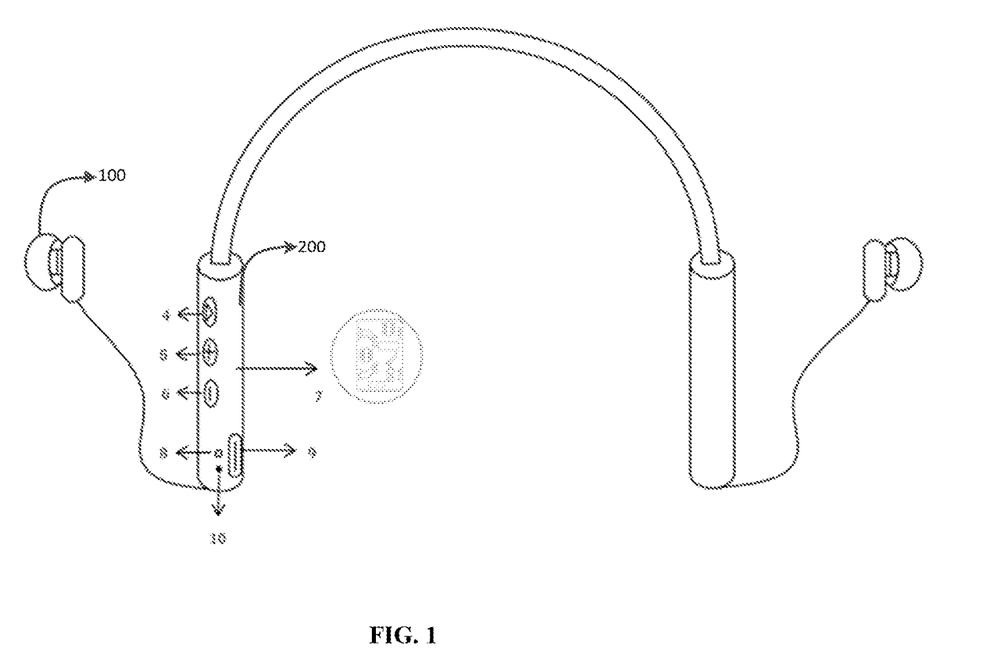
FIG. 1 is a schematic diagram of an integral structure of a neck-hanging headset according to one embodiment of the present disclosure.
Figure 2:
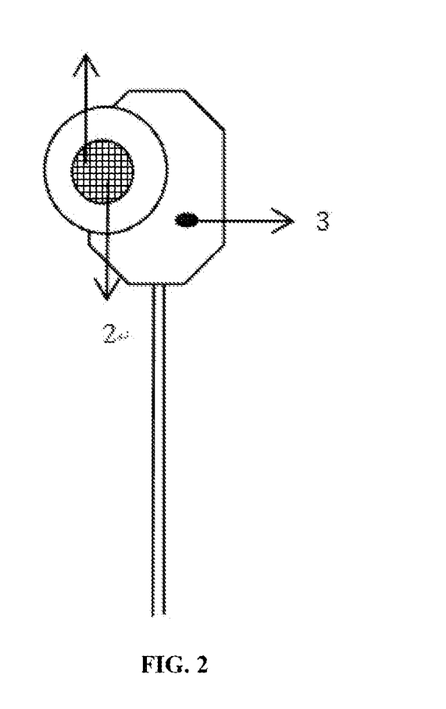
FIG. 2 is a schematic structural diagram of an earplug part of a smart headset according to one embodiment of the present disclosure.

Reference is made to FIG. 1 and FIG. 2 by taking an in-ear headset provided with a neck-hanging coil as an example to give a description, wherein the earplug part 100 includes an headset speaker 1, a microphone 2 hidden in the earplug, and a wearing detection sensor 3. In this embodiment, the headset body 200 is a neck-hanging collar, and its housing is provided with a play/pause/power key 4, a volume up key 5, a volume down key 6, a circuit board 7 encapsulated in the housing, a power indicator light 8, a Type-C interface 9, and a microphone 10. These control keys may be physical control keys or a touch panel that can be operated by touch.

In the embodiment as shown in FIG. 1, the smart headset includes at least two microphones, where the microphone 2 is configured to obtain a sound signal in an ear canal, and the microphone 10 is a microphone of the headset itself. The housing of the headset body 200 may be further provided with a microphone key for activating the sound detection microphone in the ear canal.

In the embodiment as shown in FIG. 1, an internal microphone and an external microphone are used, and the internal microphone is configured to collect a heart sound signal. However, it is to be noted that the present disclosure is not limited to this dual-microphone solution. In other embodiments, a technology of integrating the speaker with the microphone may also be used. That is, there is only one electronic unit inside the earplug, and this electronic unit not only can be used as the speaker, but also can be used as the microphone.

The circuit board 7 can integrate with a sound signal amplification circuit, a communication module, and a microcontroller (MCU). These modules may exist in the form of independent modules or may be integrated on the same circuit board. The present disclosure is not limited thereto. The communication module is configured to communicate with external smart terminals in a wired or wireless manner (such as Bluetooth). The external smart terminals include, but are not limited to, mobile phones, tablet computers, MP3 and other electronic devices.

The wearing detection sensor 3 is configured to detect whether the headset is properly worn, and the wearing detection sensor 3 may be a contact detection sensor, a capacitive sensor, or a photoelectric sensor, etc. For example, a capacitive sensing sensor is arranged, and when the earplug part is close to an ear, it is determined whether the in-ear headset has been properly worn according to the capacitance variation in the capacitive sensing sensor. For another example, the photoelectric sensor is arranged to detect whether the in-ear headset is successfully worn according to the variation in an output signal caused by the variation in light intensity. Preferably, in the embodiments of the present disclosure, the photoelectric sensor is arranged obliquely below the in-ear earplug part. In short, the working principle and working process of the smart headset provided by the embodiments of the present disclosure are as below. After a user inserts the in-ear headset into the ear canal, the photoelectric sensor on the headset detects that the user wears the headset, and a sound signal in the ear canal is collected using the microphone arranged in the earplug part. The speaker can also play music normally when the headset collects sound in the ear canal. The sound signal collected by the microphone from the ear canal is amplified by an amplification circuit, and then the amplified sound signal is outputted to the microcontroller. The sound data obtained is transmitted by the microcontroller via the communication module to an external smart terminal, such that the smart terminal processes (such as framing, filtering, etc.) the sound signal in the ear canal, and extracts a heart sound signal to obtain a heart sound signal characteristic, and inputs the heart sound signal characteristic into a pre-trained identity recognition model to categorize the heart sound signal characteristic and determine whether the individual heart sound signal characteristic belongs to a registered user (i.e., a legitimate user), and compares a determination result with a previously obtained result of a registered user to implement user authentication and device unlocking functions. After the device is unlocked, the heart sound signal characteristic is inputted into a pre-trained emotion recognition model to categorize the heart sound signal characteristic and obtain the user's current emotional state, and the user's current emotional state is recorded and archived to generate an emotion monitoring report.

Specifically, the process of performing identity authentication and emotion monitoring using the smart headset provided by the present disclosure includes a registration process of use by the user for the first time (to achieve identity authentication and emotion monitoring, the user is required to enter his/her heart sound data for model training before using the smart headset) and a process of identity authentication and emotion monitoring in actual use.

Figure 3:
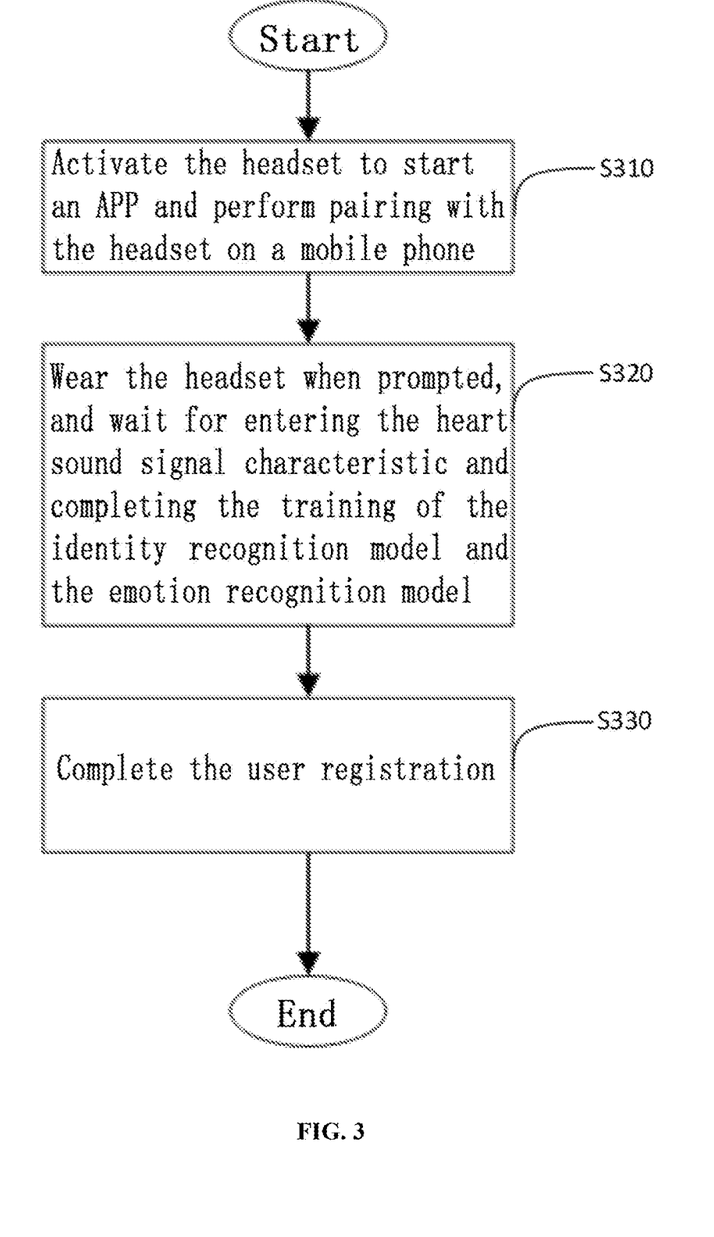
FIG. 3 is a flowchart showing user registration according to one embodiment of the present disclosure.

With reference to FIG. 3, the registration process of use by the user for the first time includes following steps.

In Step S310, the headset is activated to start an APP and perform pairing with the headset on a mobile phone.

For example, the user activates the headset, starts the APP of the mobile phone and performs Bluetooth device pairing.

In Step S320, when prompted, the headset is worn, and it is waited for entering the heart sound signal characteristic and completing the training of the identity recognition model and the emotion recognition model.

When prompted, the headset is worn, and it is waited for entering the heart sound characteristic and completing the training of the recognition models. It is to be understood that the identity recognition model and the emotion recognition model may be trained online or trained offline, and then are integrated into the headset to speed up the registration process.

It is to be noted that the user may select the emotion recognition model using a general-purpose emotion recognition model built in a system for training the emotion recognition model instead of using the user's own heart sound signal, to speed up the registration process.

The general-purpose emotion recognition model may be obtained by training pre-collected heart sound characteristics and emotional state tags of other different users (not currently registered users).

In Step S330, the user registration is completed.

After the user registration is completed, the smart headset can be used by the user normally.

Figure 4:
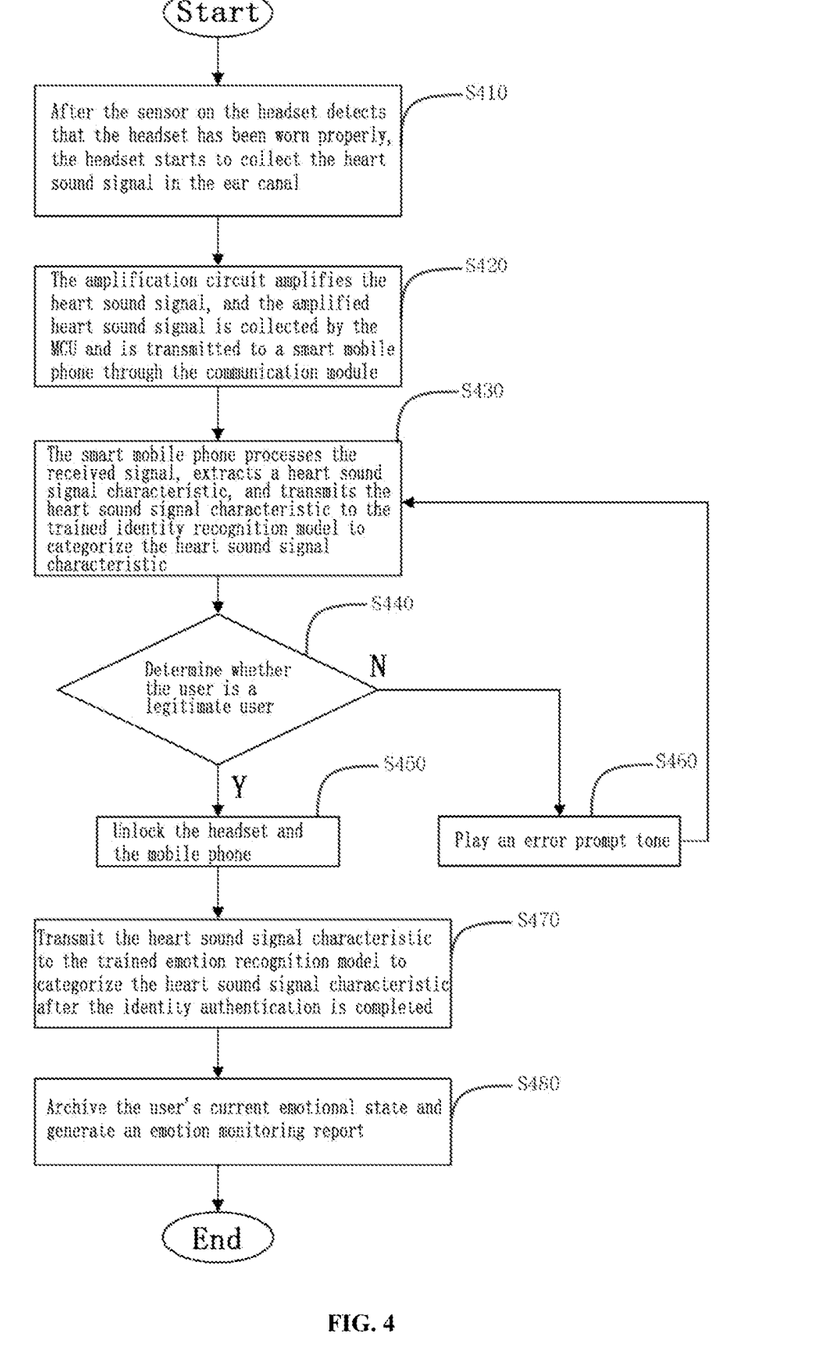
FIG. 4 is a flowchart showing identity authentication and emotion monitoring according to one embodiment of the present disclosure.

With reference to FIG. 4, the process of identity authentication and emotion monitoring in actual use includes following steps.

In Step S410, after the sensor on the headset detects that the headset has been worn properly, the headset starts to collect the heart sound signal in the ear canal.

In the actual use, the user only needs to wear the headset properly, and the headset will automatically recognize whether the headset is in a proper wearing state through the photoelectric sensor.

In Step S420, the amplification circuit amplifies the heart sound signal, and the amplified heart sound signal is collected by the MCU and is transmitted to a smart mobile phone through the communication module.

The heart sound signal obtained by the microphone is amplified by the amplification circuit, and then the amplified heart sound signal is collected by the MCU. Next, the amplified heart sound signal is transmitted to the smart mobile phone through the communication module such as a Bluetooth module.

In Step S430, the smart mobile phone processes the received signal, extracts a heart sound signal characteristic, and transmits the heart sound signal characteristic to the trained identity recognition model to categorize the heart sound signal characteristic.

After receiving the data, the smart mobile phone processes the data by, for example, framing, filtering and characteristic extraction, and then transmits the processed data to the pre-trained identity recognition model to categorize the processed data.

In Step S440, it is determined whether the user is a legitimate user.

The obtained result is matched with a stored legitimate user tag to determine whether the user is the legitimate user.

If the user is the registered legitimate user, the headset is unlocked and the mobile phone is unlocked (Step S450). If the user is determined to be an illegitimate user, an error prompt tone may be played (Step S460).

In Step S470, after the identity authentication is completed, the heart sound signal characteristic is transmitted to the trained emotion recognition model to categorize the heart sound signal characteristic.

If the headset is unlocked and the mobile phone is unlocked (Step S450), the characteristic extracted in Step S430 is transmitted to the pre-trained emotion recognition model to categorize the characteristic. After obtaining the output, the smart mobile phone will archive the user's current emotional state and generate an emotion monitoring report (Step S480).

Figure 5:
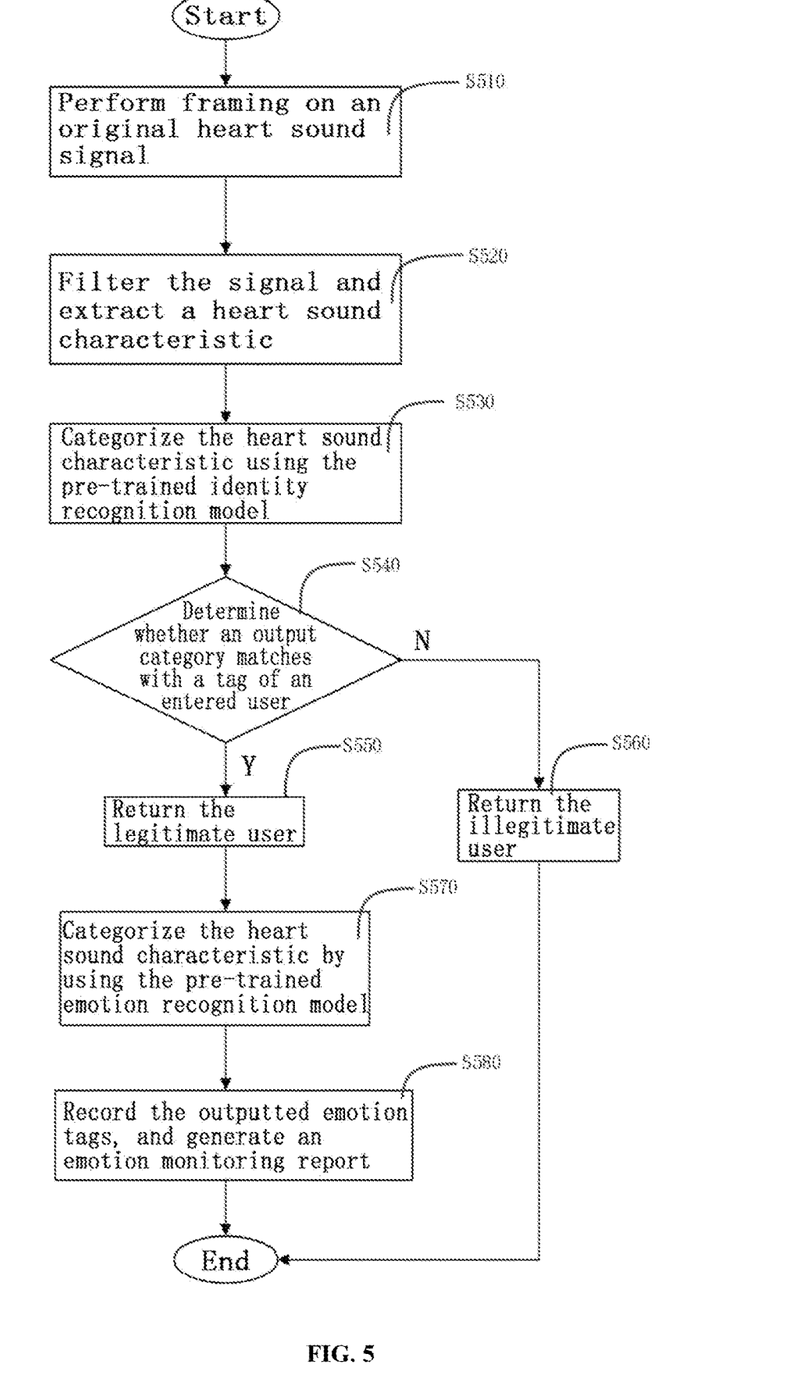
FIG. 5 is a flowchart showing identity authentication and emotion monitoring algorithms according to one embodiment of the present disclosure.

In one embodiment, with reference to FIG. 5, the process of identity authentication and emotion monitoring algorithms includes following steps.

In Step S510, framing is performed on an original heart sound signal.

For example, the mobile phone frames the received data using a Hamming window function.

In Step S520, the signal is filtered and a heart sound characteristic is extracted.

The sound signal in each window is filtered to obtain the heart sound signal. The user is likely playing music at the same time, and thus the collected original sound signal may likely be a signal obtained by mixing heart sound and other sounds. The sound signal needs to be filtered to extract a signal corresponding to the heart sound. An adult's heart rate ranges between 40 BPM and 100 BPM, and may reach up to 220 BPM during exercise. A sampling rate of the microphone is 44.1 KHz, and it has been verified that noise can be effectively filtered out by arranging a reasonable band-pass filter. In addition, the heart sound signal may also be extracted by using in combination with wavelet filtering and mean filtering, etc.

In the embodiments of the present disclosure, the sound data is framed by using the Hamming window function, and then the sound signal in each window is filtered. In this way, the signal corresponding to the heart sound can be accurately extracted, and the accuracy of subsequent categorization can be enhanced.

Further, characteristic extraction is performed on the heart sound signal. For example, a time domain characteristic and a frequency domain characteristic are extracted using time-frequency transform technologies. The time-frequency transform technologies include fast Fourier transform, short-time Fourier transform, Wigner-Ville Distribution (WVD), and wavelet transform, etc. The extracted heart sound signal characteristic includes, but is not limited to, a time-frequency diagram, a Mel spectrum coefficient, a Mel frequency cepstrum coefficient, a zero-crossing rate, a root mean square, a spectral entropy, as well as time-domain waveform characteristics such as P wave, R wave, T wave, S wave, and the original sound signal.

In Step S530, the heart sound characteristic is categorized using the pre-trained identity recognition model.

The pre-trained identity recognition model may be a binary categorizer. Specifically, the extracted heart sound signal characteristic is categorized using a categorizer trained according to the registered user data, and an output tag is obtained. Next, it is determined whether the output tag is consistent with the registered user. In this way, the identity authentication is completed.

In the present disclosure, the identity recognition model can use a deep learning model such as a support vector machine (SVM) or a convolutional neural network (CNN) and a recurrent neural network (RNN), or use other machine learning methods such as random forest, and K-nearest neighbor algorithm (KNN), etc. The present disclosure does not limit types and specific structures of the identity recognition model.

In the embodiments of the present disclosure, the categorizer is trained by machine learning for distinguishing the legitimate user from unauthorized users, which can accurately and quickly perform identity authentication.

In Step S540, it is determined whether an output category matches with a tag of an entered user.

An identity authentication result is determined according to the output category of the identity recognition model. That is, it is returned the legitimate user (Step S550), or it is returned the illegitimate user (Step S560).

In Step S570, the heart sound characteristic is categorized by using the pre-trained emotion recognition model.

The pre-trained emotion recognition model may be a categorizer that implements multiple categorizations. Specifically, the extracted heart sound signal characteristic is categorized using a categorizer trained according to the registered user data or a general-purpose emotion categorizer built in the system, and output tags are obtained, wherein the output tags represent different emotional states.

In the present disclosure, the emotion recognition model may use a deep learning model such as a support vector machine (SVM) or a convolutional neural network (CNN) and a recurrent neural network (RNN), or use other machine learning methods such as random forest, and K-nearest neighbor algorithm (KNN), etc. The emotional states include, for example, happiness, sadness, anger, fear, and normal, etc. The present disclosure does not limit types and specific structures of the emotion recognition model and categories of the emotional states.

In the embodiments of the present disclosure, the user's emotional state is obtained by training the categorizer through machine learning, which can accurately perform emotion monitoring. It is to be noted that the user's physiological health can also be monitored based on the heart sound signal characteristic.

In Step S580, the outputted emotion tags are recorded, and an emotion monitoring report is generated.

The current emotional state of the user is determined and archived according to the output tags of the emotion recognition model to generate the emotion monitoring report.

It is to be understood that traditional functions (i.e., voice conversation and music playback, etc.,) of the smart headset provided by the present disclosure can be implemented by using related technical solutions disclosed, which is not unnecessarily elaborated any more herein.

To further verify effects of the present disclosure, the inventors implement the design of a prototype machine. Experiments have proved that for 50 registered users, this identity authentication method can reach categorization accuracy as high as 95%. The emotion recognition model trained according to the registered user data can reach recognition accuracy as high as 90% for four types of emotions, and the general-purpose emotion recognition model can reach recognition accuracy as high as 70% for the four types of emotions, which can fully meet requirements for daily applications.

In summary, the smart headset provided by the present disclosure has the functions and shapes of ordinary headsets. However, the smart headset provided by the present disclosure can achieve the identity authentication and emotion monitoring based on a heart sound signal without additional electrodes, and thus will not cause any interference to the user during the operation of the device. The smart headset is lower in hardware costs, convenient to carry and use, and strong in robustness. As long as the user wears the headset as usual, the identity authentication and emotion monitoring can be quickly and autonomously performed while the user's privacy is protected, and the headset device is unlocked, and even a smart device (such as a mobile phone, a computer, and a wearable device, etc.) paired with the headset is further unlocked. Therefore, the smart headset is suitable for daily use.

The present disclosure may be a system, a method, and/or a computer program product. The computer program product may include a computer readable storage medium having computer readable program instructions thereon for causing a processor to carry out aspects of the present disclosure.

The computer readable storage medium may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. More specific examples (a non-exhaustive list) of the computer readable storage medium include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. The computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical fiber transmission, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

The computer program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In a scenario involved with the remote computer, the remote computer may be coupled to the user's computer through any type of network, including a local area network (LAN) or a wide area network (WAN), or may be coupled to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described with reference to flowcharts and/or block diagrams according to the method, apparatus (system) and a computer program product of the embodiments of the present disclosure. It is to be understood that each block of the flowcharts and/or block diagrams, and combinations of blocks in the flowcharts and/or block diagrams, can be implemented by the computer readable program instructions.

These computer readable program instructions may be provided to a processor of a general purpose computer, special purpose computer, or other programmable data processing apparatus to produce a machine, such that these instructions, which execute via the processor of the computer or other programmable data processing apparatus, create means for implementing the functions/acts specified in one or more blocks in the flowcharts and/or block diagrams. These computer readable program instructions may also be stored in a computer readable storage medium that can direct a computer, a programmable data processing apparatus, and/or other devices to function in a particular manner, such that the computer readable medium having instructions stored therein includes an article of manufacture including instructions which implement aspects of the function/act specified in one or more blocks in the flowcharts and/or block diagrams.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in one or more blocks in the flowcharts and/or block diagrams.

The flowcharts and block diagrams in the accompanying drawings illustrate architectures, functions and operations of possible implementations of systems, methods, and computer program products according to a plurality of embodiments of the present disclosure. In this regard, each block in the flowcharts or block diagrams may represent a module, a program segment, or a portion of instructions, which includes one or more executable instructions for implementing the specified logical function(s). In some alternative implementations, the functions denoted in the blocks may occur in a sequence different from the sequences shown in the accompanying drawings. For example, two blocks shown in succession may, in fact, be executed substantially concurrently, or the blocks may sometimes be executed in a reverse sequence, depending upon the functions involved. It is also to be noted that each block in the block diagrams and/or flowcharts and/or a combination of the blocks in the block diagrams and/or flowcharts may be implemented by a special-purpose hardware-based system executing specific functions or acts, or by a combination of a special-purpose hardware and computer instructions. It is well known to those skilled in the art that implementations by means of hardware, implementations by means of software and implementations by means of software in combination with hardware are equivalent.

The descriptions of the various embodiments of the present disclosure have been presented above for purposes of illustration, but are not intended to be exhaustive or limited to the embodiments disclosed. Therefore, it is apparent to an ordinary skilled person in the art that modifications and variations could be made without departing from the scope and spirit of the embodiments. The terminology used herein is chosen to best explain the principles of the embodiments, the practical application or technical improvement over technologies found in the marketplace, or to enable others of ordinary skill in the art to understand the embodiments disclosed herein. The scope of the present disclosure is limited by the appended claims.

What is claimed is:

1. A method for a user recognition and an emotion monitoring based on a smart headset, wherein the smart headset comprising an earplug part and a main body, the earplug part is provided with a first microphone and a wearing detection sensor, and a housing of the main body is internally provided with a signal amplification circuit, a communication module, and a microcontroller, wherein the method comprises
   detecting whether the user wears the smart headset properly by the wearing detection sensor,
   obtaining a sound signal in an ear canal by the first microphone,
   amplifying the sound signal by the signal amplification circuit to obtain an amplified sound signal,
   outputting the amplified sound signal is outputted to the microcontroller,
   transmitting the amplified sound signal by the microcontroller via the communication module to a smart terminal paired with the smart headset to extract a heart sound signal characteristic,
   validating a legality of an identity of the user and
   inferring a current emotional state of the user according to the heart sound signal characteristic;
   wherein the step of validating the legality of the identity of the user and inferring the current emotional state of the user according to the heart sound signal characteristic comprises steps of:
   collecting an original sound signal in the ear canal by using the first microphone arranged in the earplug part;
   amplifying the original sound signal to obtain the amplified sound signal in the ear canal;
   processing the amplified sound signal in the ear canal and extracting the heart sound signal characteristic, inputting the heart sound signal characteristic into a pre-trained identity recognition model for an identity authentication, and inputting the heart sound signal characteristic into a pre-trained emotion recognition model for an emotional categorization; and
   determining whether to unlock the smart headset and whether to unlock the smart terminal paired with the smart headset according to an identity authentication result, and determining the user's current emotional state of the user according to an emotional categorization result to generate an emotion monitoring report.

2. The method according to claim 1, wherein the housing of the main body is provided with a key for activating the first microphone to collect a sound in the ear canal.

3. The method according to claim 1, wherein the smart headset is an in-ear headset, an ear-hanging headset or a neck-hanging headset.

4. The method according to claim 3, wherein the wearing detection sensor is a photoelectric sensor and the wearing detection sensor is arranged obliquely below an in-ear earplug part.

5. The method according to claim 1, wherein the housing of the main body is provided with one or more of a tuning key, a power key, a play key, and a pause key.

6. The method according to claim 1, wherein the housing of the main body is further internally provided with a second microphone configured to implement communications.

7. The method according to claim 1, wherein the earplug part is further provided with a speaker, and the speaker and the first microphone are of an integrated design.

8. The method according to claim 1, wherein the step of processing the amplified sound signal in the ear canal and extracting the heart sound signal characteristic comprises steps of:
   framing the amplified sound signal in the ear canal by using a Hamming window function;
   denoising the amplified sound signal in each window through filtering to obtain a heart sound signal; and
   extracting a time-domain characteristic and a frequency-domain characteristic from the heart sound signal through a time-frequency transformation, and combining the time-domain characteristic and the frequency-domain characteristic into the heart sound signal characteristic.

9. The method according to claim 8, wherein the step of denoising the amplified sound signal in the each window through filtering comprises:
   denoising using a band-pass filter based on a heart rate of the user and a sampling frequency of the first microphone.

10. The method according to claim 1, wherein a training process of the pre-trained identity recognition model comprises:
    collecting a first heart sound signal of a headset user and a second heart sound signal of a non-user and extracting heart sound characteristics from the first heart sound signal and the second heart sound signal to construct a training sample set; and
    training an identity recognition model by taking the heart sound characteristics of the training sample set as an input and a type of a corresponding user or non-user as an output to obtain a binary categorizer for distinguishing a legitimate user and an unauthorized user.

11. The method according to claim 1, wherein a training process of the pre-trained emotion recognition model comprises:
    collecting heart sound signals of a headset user in different emotional states and extracting heart sound characteristics from the heart sound signals to construct a training sample set; and training an emotion recognition model by taking the heart sound characteristics of the training sample set as an input and types of corresponding emotional states as an output to obtain a categorizer for inferring the current emotional state of the user.

12. A non-transitory computer-readable storage medium, storing a computer program, wherein when the computer program is executed by a processor, the computer program implements steps of the method according to claim 1.

13. The non-transitory computer-readable storage medium according to claim 12, wherein the housing of the main body is provided with a key for activating the first microphone to collect a sound in the ear canal.

14. The non-transitory computer-readable storage medium according to claim 12, wherein the smart headset is an in-ear headset, an ear-hanging headset or a neck-hanging headset.

15. The non-transitory computer-readable storage medium according to claim 14, wherein the wearing detection sensor is a photoelectric sensor and the wearing detection sensor is arranged obliquely below an in-ear earplug part.

16. The non-transitory computer-readable storage medium according to claim 12, wherein the housing of the main body is provided with one or more of a tuning key, a power key, a play key, and a pause key.

17. The non-transitory computer-readable storage medium according to claim 12, wherein the housing of the main body is further internally provided with a second microphone configured to implement communications.

18. The non-transitory computer-readable storage medium according to claim 12, wherein the earplug part is further provided with a speaker, and the speaker and the first microphone are of an integrated design.

19. An electronic device, comprising a memory and a processor, a computer program capable of running in the processor is stored in the memory, wherein when the processor executes the computer program, steps of the method according to claim 1 are implemented.

* * * * *